United States Patent
Schwartz et al.

(10) Patent No.: US 6,221,057 B1
(45) Date of Patent: Apr. 24, 2001

(54) HEMOSTASIS VALVE, SYSTEM AND ASSEMBLY

(75) Inventors: Robert S. Schwartz; David R. Holmes, both of Rochester, MN (US); David Berry, Longmont; Donald G. Ellis, Boulder, both of CO (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 09/240,743

(22) Filed: Jan. 29, 1999

Related U.S. Application Data

(62) Division of application No. 08/735,521, filed on Oct. 23, 1996, now Pat. No. 5,895,376.

(51) Int. Cl.[7] .................................................. A61M 25/00
(52) U.S. Cl. .......................................... 604/246; 604/537
(58) Field of Search .................................... 604/246, 523, 604/533, 537, 264

(56) References Cited

U.S. PATENT DOCUMENTS

| | | |
|---|---|---|
| 3,276,472 | 10/1966 | Jinkens et al. . |
| 3,759,289 | 9/1973 | Dewall . |
| 4,000,739 | 1/1977 | Stevens . |
| 4,254,773 | 3/1981 | Waldbillig . |
| 4,300,571 | 11/1981 | Waldbillig . |
| 4,337,770 | 7/1982 | Young . |
| 4,580,573 | 4/1986 | Quinn . |
| 4,610,665 | 9/1986 | Matsumoto et al. . |
| 4,701,160 | 10/1987 | Lindsay et al. . |
| 4,723,550 | 2/1988 | Bales et al. . |
| 4,726,374 | 2/1988 | Bales et al. . |
| 4,743,235 | 5/1988 | Waldbillig et al. . |
| 4,798,594 | 1/1989 | Hillstead . |
| 4,886,507 | 12/1989 | Patton et al. . |
| 4,895,565 | 1/1990 | Hillstead . |
| 4,909,798 | 3/1990 | Fleischhacker et al. . |
| 4,932,114 | 6/1990 | Morse et al. . |
| 4,932,633 | 6/1990 | Johnson et al. . .......... Guest et al. . |

(List continued on next page.)

FOREIGN PATENT DOCUMENTS

| | | |
|---|---|---|
| 0 426 407 A2 | 5/1991 | (EP) . |
| 0 550 069 A1 | 7/1993 | (EP) . |
| WO 91/10459 | 7/1991 | (WO) . |
| WO 92/11880 | 7/1992 | (WO) . |

OTHER PUBLICATIONS

Brochure, "MORSE™ Y–Adaptors . . . The Largest Lumen Y–Adaptors Keep Interventional Options Open", NAMIC U.S.A. Corporation, 4 pp. (1994).
Brochure, "Medex Cath Lab Products", Medex Inc., 6 pp. (Undated).
Brochure, "Product Profile Basix25® Inflation Device", Merit Medical Systems, Inc., 2 pp. (1996).

*Primary Examiner*—John D. Yasko
(74) *Attorney, Agent, or Firm*—Merchant & Gould P.C.

(57) ABSTRACT

A hemostasis valve including a collapsible membrane in a portion of a through-lumen. Fluid pressure in a chamber surrounding the collapsible membrane assists in sealing the collapsible membrane around an operating device inserted through the hemostasis valve. Different mechanisms for mechanically deforming the collapsible membrane to assist in sealing are disclosed. Also, a system for continuously flushing a vascular catheter connected to a hemostasis valve at a rate of 0.10 to 10.0 cubic centimeters per minute, and a hemostasis valve assembly including an expandable reservoir which stores liquid volume under pressure.

14 Claims, 3 Drawing Sheets

U.S. PATENT DOCUMENTS

| | | |
|---|---|---|
| 4,946,133 | 8/1990 | Johnson et al. . |
| 4,960,412 | 10/1990 | Fink . |
| 5,000,745 | 3/1991 | |
| 5,041,095 | 8/1991 | Littrell . |
| 5,071,411 | 12/1991 | Hillstead . |
| 5,078,433 | 1/1992 | Morse et al. . |
| 5,092,857 | 3/1992 | Fleischhacker . |
| 5,098,406 | 3/1992 | Sawyer . |
| 5,102,395 | 4/1992 | Cheer et al. . |
| 5,158,553 | 10/1992 | Berry et al. . |
| 5,161,773 | 11/1992 | Tower . |
| 5,171,230 | 12/1992 | Eland et al. . |
| 5,209,732 | 5/1993 | Lampropoulos et al. . |
| 5,215,536 | 6/1993 | Lampropoulos et al. . |
| 5,267,966 | 12/1993 | Paul . |
| 5,356,375 | 10/1994 | Higley . |
| 5,356,379 | 10/1994 | Vaillancourt . |
| 5,389,080 | 2/1995 | Yoon . |
| 5,405,334 | 4/1995 | Roth et al. . |
| 5,429,609 | 7/1995 | Yoon . |
| 5,441,487 | 8/1995 | Vedder . |
| 5,456,676 | 10/1995 | Nelson et al. . |
| 5,514,109 | 5/1996 | Mollenauer et al. . |
| 5,542,931 | 8/1996 | Gravener et al. . |
| 5,634,911 | 6/1997 | Hermann et al. . |
| 5,782,817 | 7/1998 | Franzel et al. . |

HEMOSTASIS VALVE, SYSTEM AND ASSEMBLY

This application is a Divisional of application Ser. No. 08/735,521, filed Oct. 23, 1996, which application is incorporated herein by reference, now U.S. Pat. No. 5,895,376.

FIELD OF THE INVENTION

This invention relates generally to hemostasis valves used in diagnostic, therapeutic and interventional vascular procedures, and more particularly to the sealing mechanisms in such devices and to related systems, including those for flushing.

BACKGROUND OF THE INVENTION

Hemostasis valves (also sometimes referred to as "Y-connectors" and "Touhy-Borst valves") are commonly used in certain medical procedures. A guide catheter is connected to the distal end of the valve, and an operating instrument, such as a guide wire or balloon catheter, is inserted into the proximal end and through the guide catheter to the desired location in the patient. After the operating instrument is in place, the valve is closed to keep blood from leaking out of the patient ("hemostasis").

One of the problems with current hemostasis valves is that they are cumbersome to operate, taking a long time to open and close. Most employ a Touhy-Borst sealing mechanism such as that described in U.S. Pat. No. 4,886,507. A threaded cap deforms an O-ring into a tapered opening until the O-ring clamps down on the operating instrument. Each time the operating instrument is adjusted, the cap must be unthreaded before and then rethreaded after the manipulation. During the time that the valve is open, blood leaks from the patient and/or contrast media is lost. Inaccurate blood pressure readings also occur. There is also a risk of air emboli when the valve is open, particularly when removing the operating instrument.

Another problem with prior art hemostasis valves, such as Touhy-Borst valves, is that significant mechanical force must be applied to the operating instrument in order to maintain the seal. This is particularly a problem at higher system pressures, and when pressure spikes occur, such as when flushing the system with saline or introducing contrast media. The often delicate drive shaft of the operating instrument can be crushed by the force of the seal. The high force seal also prevents moving the operating instrument while the valve is closed.

One attempt at addressing some of these problems is shown in the '507 patent. In addition to a Touhy-Borst, this design includes a membrane having a fixed circular opening for sealing shafts within a certain diameter range. This sealing arrangement, however, still relies solely on a mechanical sealing system which requires high shaft forces at high system pressures. It also incorporates the same threaded Touhy-Borst valve, which requires the cap to be manually threaded in order to close the valve. The fixed opening membrane would also be helpful only with operating instruments in a particular diameter range.

Hemostasis systems typically have a perfusion port used to flush the system with saline in order to prevent blood clots from being formed. This is done by a technician periodically during the procedure, which takes time and may interrupt the procedure. The blood pressure readings are also inaccurate during the flush.

What has been needed is a hemostasis valve which opens and closes easier, maintains a seal at higher pressures without damaging the instrument, and permits movement of the instrument while maintaining a seal. What has also been needed is a hemostasis system which reduces or eliminates the need for periodic flushing. What has also been needed is a hemostasis assembly which reduces blood loss and the risk of air emboli while the valve is open.

SUMMARY OF THE INVENTION

According to the present invention, a hemostasis valve, system and assembly are provided. The inventions can be used in a variety of diagnostic, therapeutic and interventional procedures, including angiography, angioplasty, stent placement, drug infusion, intravascular ultrasound, rotablation, and atherectomy.

In one aspect of the invention, a hemostasis valve comprises a valve body having a proximal end for receiving an operating device, a distal end for connection to a guide catheter, and a through-lumen in the valve body intermediate the proximal and distal ends. The operating device is inserted through the through-lumen and into the guide catheter. A chamber in the valve body surrounds the through-lumen and is filled with fluid under pressure. A collapsible membrane in a portion of the through-lumen is constructed and arranged such that the fluid pressure in the chamber assists in sealing the collapsible membrane around the operating device.

In another aspect of the invention, a hemostasis valve comprises a valve body having a proximal end for receiving an operating device, a distal end for connection to a guide catheter, and a through-lumen in the valve body intermediate the proximal and distal ends. The operating device is inserted through the through-lumen and into the guide catheter. The through-lumen comprises a proximal portion, a distal portion and an elastomeric sleeve therebetween. One of the proximal and distal portions of the through-lumen is rotatable relative to the valve body between a closed position wherein the elastomeric sleeve is twisted to seal around the operating device and an open position wherein the elastomeric sleeve is sufficiently untwisted to unseal the elastomeric sleeve from the operating device.

In another aspect of the invention, a system for flushing a vascular catheter comprises a hemostasis valve and a vascular catheter for insertion into a patient, sealingly connected to the hemostasis valve. A source for providing flushing fluid under pressure is in fluid communication with the hemostasis valve. A mechanism controls the flow of said flushing fluid from the source to the hemostasis valve at a rate of about between 0.10 to 10.0 cubic centimeters per minute, thereby continuously flushing the vascular catheter.

In another aspect of the invention, a hemostasis valve assembly comprises a hemostasis valve which is moveable between a closed position wherein liquid in fluid communication with a patient is sealed and an open position. An expandable reservoir in fluid communication with the liquid in the hemostasis valve is moveable between expanded and retracted positions. The expandable reservoir is constructed and arranged such that, when the hemostasis valve is moved to the open position, the expandable reservoir retracts toward the retracted position so as to force liquid out of the open hemostasis valve.

These and other advantages and features of novelty which characterize the invention are pointed out with particularity in the claims annexed hereto. However, for a better understanding of the invention and its advantages, reference should be made to the drawings which form a further part hereof, and to the accompanying descriptive matter in which there is illustrated and described preferred embodiments of the invention.

DETAILED DESCRIPTION OF THE PREFERRED EMBODIMENTS

Figure 1:
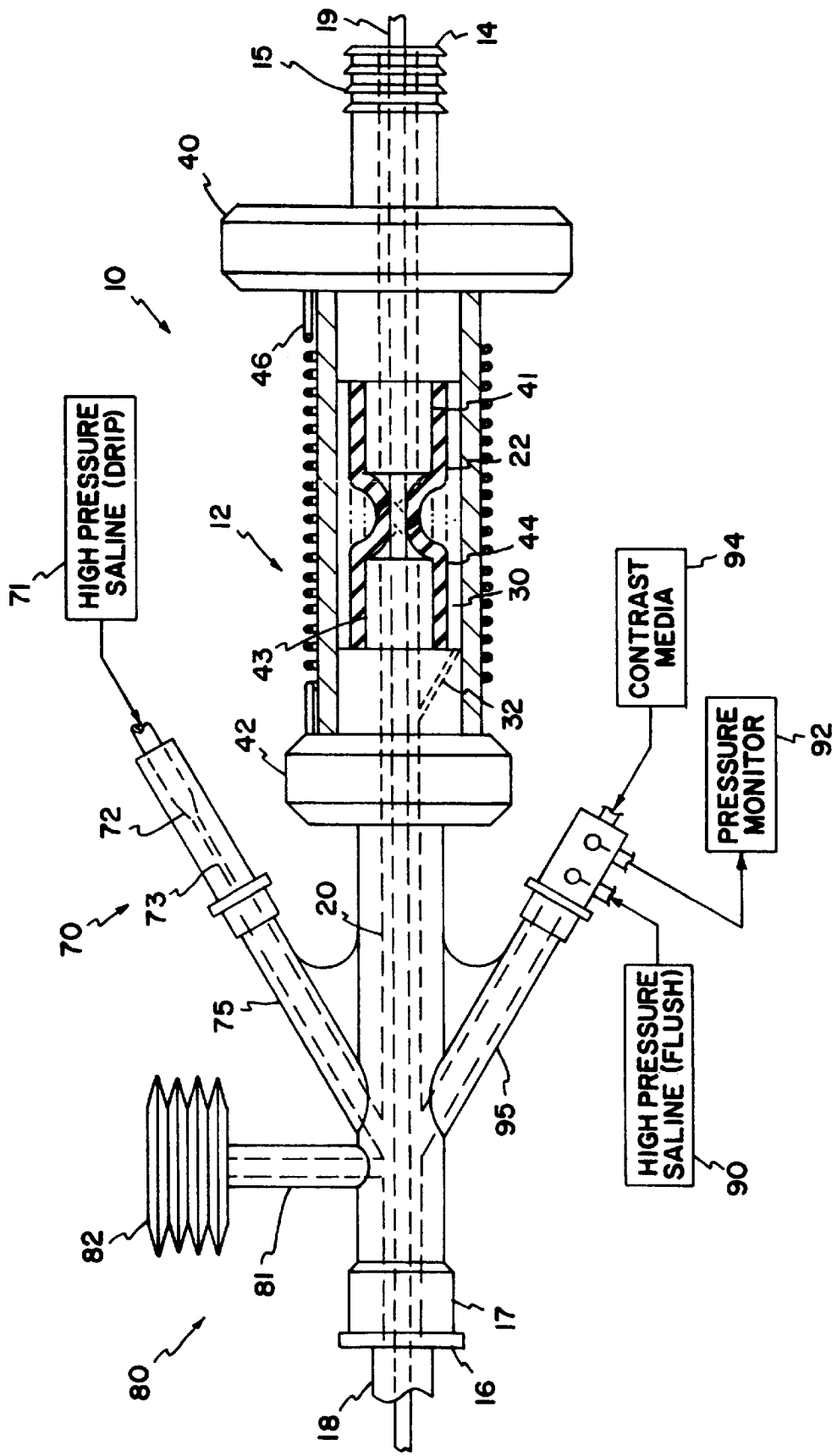
FIG. 1 is a partial cross-sectional view of a first embodiment of a hemostasis valve according to the present invention, including a system for continuously flushing a vascular catheter and an expandable reservoir.
Figure 2:
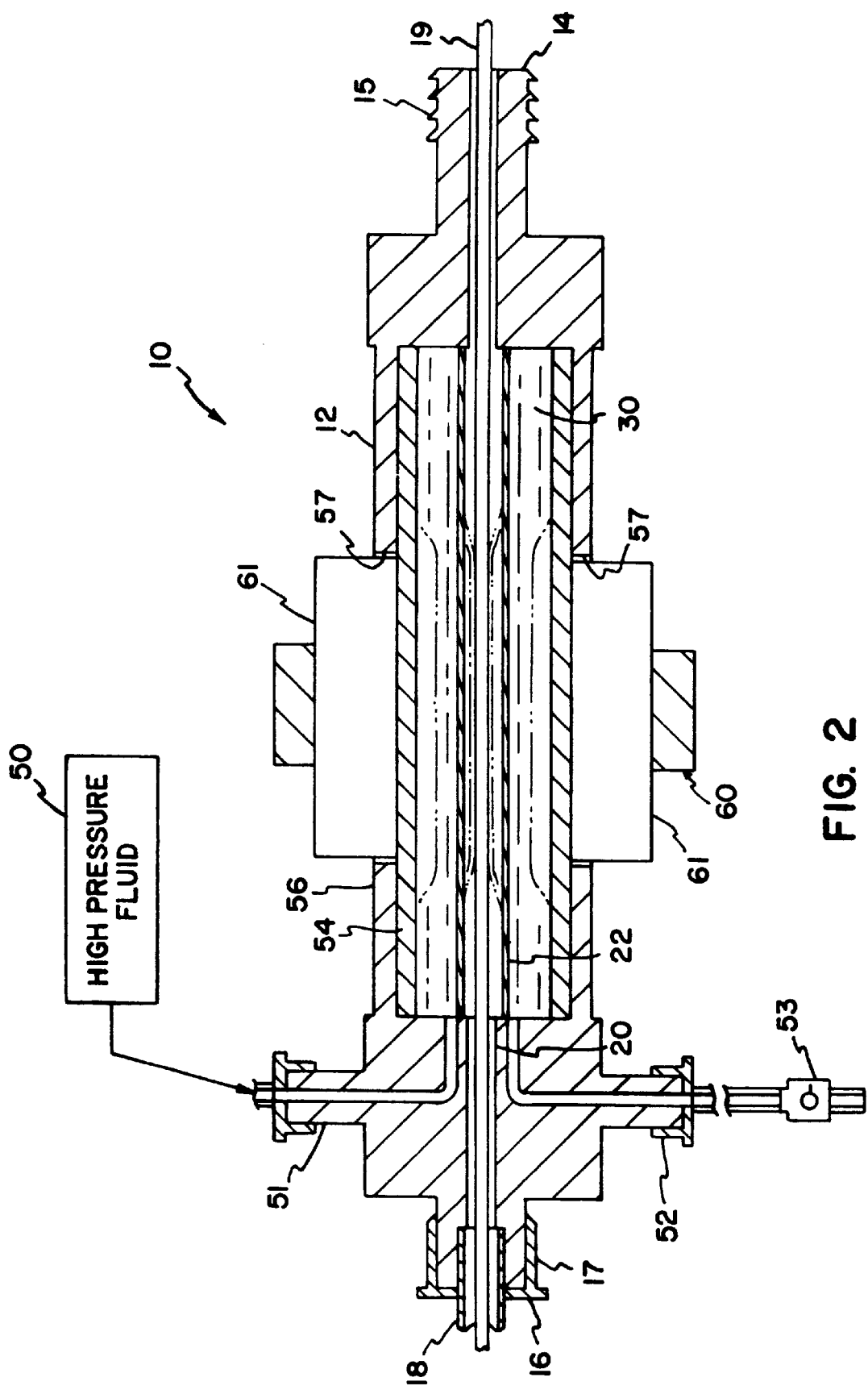
FIG. 2 is a cross-sectional view of a second embodiment of a hemostasis valve according to the present invention.
Figure 3:
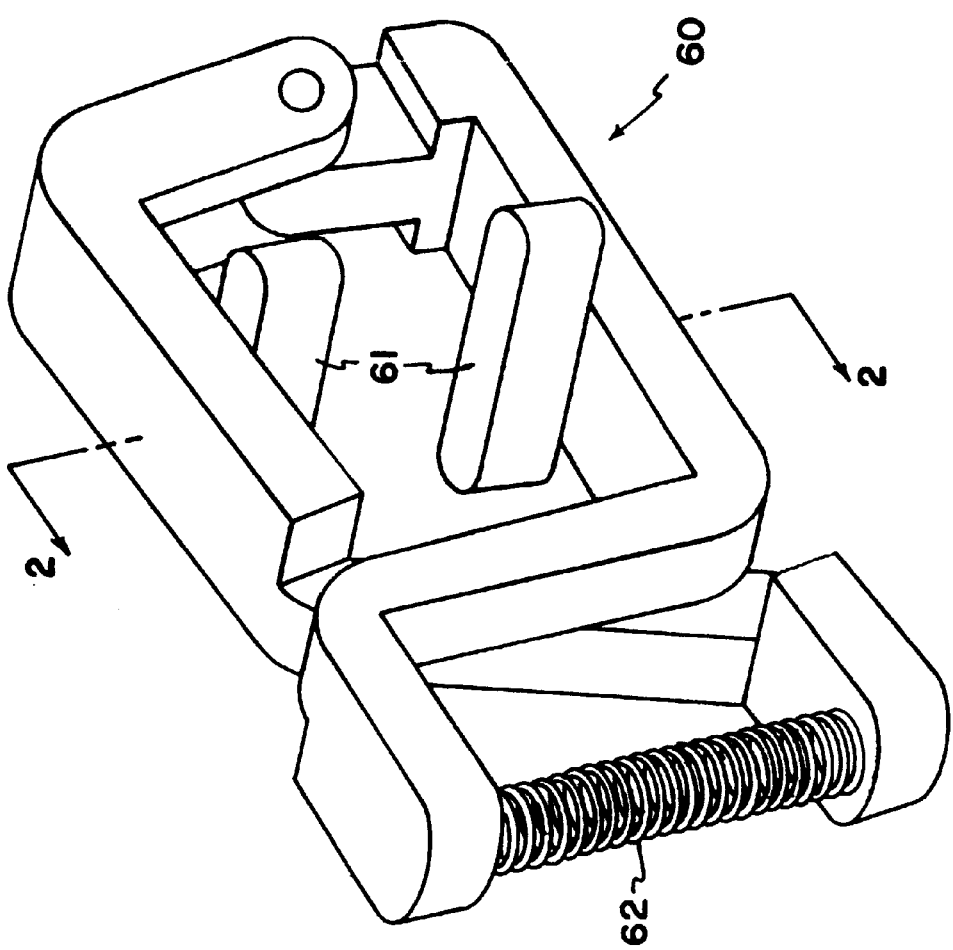
FIG. 3 is a perspective view of the clamp used in the hemostasis valve of FIG. 2.

Referring now to the drawings, wherein like numerals designate like parts, first and second hemostasis valve embodiments are shown in FIG. 1 and FIGS. 2–3, respectively. The hemostasis valves of the present invention can be used with a variety of diagnostic, therapeutic, and interventional operating devices as set forth above.

Referring to the first embodiment shown in FIG. 1, hemostasis valve 10 comprises valve body 12 with proximal end 14 for receiving operating device 19 and distal end 16 for connection to guide catheter 18. A standard hose barb 15 is shown at proximal end 14 and a standard luer lock 17 is shown at distal end 16 for connection to guide catheter 18.

Valve body 12 includes through-lumen 20 through which operating device 19 is received. In a portion of through-lumen 20 is a collapsible membrane 22 which seals around operating device 19. This sealing is assisted by fluid pressure from chamber 30 surrounding through-lumen 20. This pressure assist is advantageous in a number of ways. The lower pressure differential between through-lumen 20 and chamber 30 makes it easier to create a seal by mechanically deforming collapsible membrane 22. Less mechanical force is consequently necessary for sealing, which reduces the risk of damaging the drive shaft of the operating device and helps permit manipulation of operating device 19, longitudinally and torsionally, while maintaining a seal.

In the first embodiment of FIG. 1, chamber 30 is in fluid communication with through-lumen 20 through passage 32. Thus, for example saline or the patient's blood can pass back and forth. This arrangement is particularly helpful in dynamic high pressure situations because the high pressure tending to open the hemostasis valve is offset by the also high pressure in chamber 30.

Collapsible membrane 22 is mechanically deformed in the first embodiment by turning adjustment knob 40 so as to twist elastomeric sleeve 44 around operating device 19 to effect a seal. Adjustment knob 40 is biased toward the closed position (shown) by coil spring 46 around valve body 12 which is connected at its opposite end to stationary knob 42. It will be understood that a variety of other spring mechanisms could be employed for this purpose. This arrangement permits better sensitivity when opening valve as well as automatic closure, which reduces the time that the valve is open.

Elastomeric sleeve 44 is fixedly and sealingly disposed onto barbs 41, 43 of adjustment and stationary knobs 40, 42. Sleeve 44 is preferably made of a flexible biocompatible material such as silicone or latex. The preferred sleeve has a 3/16 inch o.d., 1/8 inch i.d., and a length (measured between barbs 41,43) between 0.25 and 0.50 inches. To help facilitate movement of operating device 19 while maintaining the valve closed, it would be preferable to coat the inner side of sleeve 44 with for example a hydrogel to provide a slicker surface.

Referring to FIGS. 2 and 3, a second preferred embodiment of a hemostasis valve is shown. In describing the second embodiment, attention will be focused to the relevant differences from the first embodiment.

In the second embodiment, chamber 30 is not in fluid communication with through-lumen 20, but is instead isolated. Saline or other fluid is provided to chamber 30 by high pressure fluid source 50 through port 51. Second port 52 is used to evacuate air or relieve pressure from chamber 30 with valve 53. In this way, opening and closing of the hemostasis valve can in fact be accomplished solely by selectively providing sufficient fluid pressure in chamber 30 to completely seal collapsible membrane 22 around operating device 19. A third port (not shown) communicating with through-lumen 20 could be used for pressure monitoring, flushing, and/or injecting contrast media for example. The fluid pressure in chamber 30 is preferably at least that in through-lumen 20. A more simple arrangement than the second preferred embodiment would eliminate both ports 51, 52 and have a constant pressure in chamber 30 sufficient to assist in sealing collapsible membrane 22 around operating device 19.

Collapsible membrane 22 is mechanically deformed by action of feet 61 of clamp 60, best shown in FIG. 3. As with the first embodiment, a spring 62 (here a compression spring) is used to bias the valve to a closed position. Feet 61 extend into correspondingly shaped openings 57 in rigid outer wall 56 and deform outer elastomer tube 54 radially inward. This increases the fluid pressure in chamber 30 which in turn deforms collapsible membrane 22 to seal around operating device 19. Both membrane 22 and tube 54 are preferably made of latex. Membrane 22 has a 3/16 inch i.d. and is 0.012 inches thick. Tube 54 has a 3/8 inch i.d. and is 0.085 inches thick. They could also be made of silicone or urethane, but a thinner wall for tube 54 would likely be required. It will be understood that a variety of other mechanisms could be used to radially direct pressure and that mechanical pressure could be applied directly to collapsible membrane 22 alone or in combination with fluid pressure to effect a seal.

Referring now to FIG. 1, system 70 provides a continuous flush of guide catheter 18 and hemostasis valve 10. Saline is delivered to hemostasis valve 10 through first port 75 at a rate of about 0.1 to 10.0 cubic centimeters per minute, preferably about 1.0 cubic centimeters (1 ml.) per minute. High pressure saline is supplied by source 71, which is preferably a saline bag at a pressure of about 300 millimeters of mercury. The desired flow rate can be achieved by a variety of flow restricting arrangements. The preferred arrangements are an appropriately sized orifice 72 and/or capillary tube 73. The preferred capillary tube 73 is 30 gauge hypotube 0.6 inches long and having an i.d. of 0.006 inches. System 70 permits more continuous monitoring of pressure with pressure monitor 92 by reducing or possibly eliminating the need for flushing with high pressure saline 90.

Referring again to FIG. 1, hemostasis valve assembly 80 includes bellows 82 which acts as an expandable reservoir of liquid volume. Bellows 82 is connected to hemostasis valve 10 by third port 81. It is preferably made of an elastomeric material such as latex and should "saturate" (i.e., be substantially expanded) at a mean pressure of about between 60 to 120 millimeters of mercury, most preferably at a typical blood pressure of about 90 millimeters of mercury. It will be appreciated that a variety of expandable reservoir arrangements other than a bellows could be suitable for this purpose, as for example one that relies on springs or another mechanism instead of the inherent elasticity of the reservoir.

The liquid volume stored by expandable reservoir 82 under pressure has a number of advantages. It reduces blood loss when hemostasis valve 10 is opened by replacing lost liquid with liquid from the retracting reservoir instead of blood from the patient. There is also a significant risk of air emboli caused by the vacuum which is created when the distal end of operating device 19 is pulled out of proximal end 14 of hemostasis valve 10. Expandable reservoir 82 helps force liquid out of proximal end 14 of hemostasis valve 10 so as to prevent air from entering. Expanding reservoir 82 is also helpful when hemostasis valve 10 is closed. For example, it will tend to absorb pressure spikes, such as those created by high pressure flushing 90 or injecting contrast media 94, by reservoir expanding instead of liquid leaking out of hemostasis valve 10.

It should be understood that the present invention is not limited to the preferred embodiments discussed above which are illustrative only. Changes may be made in detail, especially in matters of shape, size, arrangement of parts, or material of components within the principles of the invention to the full extent indicated by the broad general meanings of the terms in which the appended claims are expressed.

We claim:

1. A system for flushing a vascular catheter, comprising:
   (a) a hemostasis valve;
   (b) a vascular catheter for insertion into a patient, sealingly connected to said hemostasis valve;
   (c) a source for providing flushing fluid under pressure, in fluid communication with said hemostasis valve; and
   (d) means for controlling the flow of said flushing fluid from said source to said hemostasis valve at a rate of about between 0.10 to 10.0 cubic centimeters per minute, thereby continuously flushing said vascular catheter.

2. A system according to claim 1, wherein said flow controlling means comprise a flow restricting orifice.

3. A system according to claim 1, wherein said flow controlling means comprise a narrow tube having a diameter and length appropriate for achieving a predetermined flow rate.

4. A system according to claim 1, further comprising a pressure monitor.

5. A system according to claim 1, further comprising means for periodically flushing said vascular catheter at a relatively high rate.

6. A system for flushing a vascular catheter, comprising:
   (a) hemostasis valve;
   (b) a vascular catheter for insertion into a patient, sealingly connected to said hemostasis valve;
   (c) a source for providing flushing fluid under pressure, in fluid communication with said hemostasis valve; and
   (d) structure defining a flow restricting orifice that controls the flow of flushing fluid from said source to said hemostasis valve at a rate of about between 0.10 to 10.0 cubic centimeters per minute, thereby continuously flushing said vascular catheter.

7. A system according to claim 6, wherein said structure comprises a narrow tube having a diameter and length appropriate for achieving a predetermined flow rate.

8. A system according to claim 6, further comprising a pressure monitor.

9. A system according to claim 6, further comprising means for periodically flushing said vascular cather at a relatively high rate.

10. A system for flushing a vascular cather, comprising:
    (a) a hemostasis valve;
    (b) a vascular catheter for insertion into a patient, sealingly connected to said hemostasis valve;
    (c) a source for providing flushing fluid under pressure, in fluid communication with said hemostasis valve;
    (d) means for controlling the flow of said flushing fluid from said source to said hemostasis valve at a rate of about between 0.10 to 10.0 cubic centimeters per minute, thereby continuously flushing said vascular catheter; and
    (e) means for periodically flushing said vascular catheter at a relatively high rate compared to said flow controlling means.

11. A system according to claim 10, wherein said flow controlling means comprise a flow restricting orifice.

12. A system according to claim 11, wherein said flow controlling means comprise a narrow tube having a diameter and length appropriate for achieving a predetermined flow rate.

13. A system according to claim 10, further comprising a pressure monitor.

14. A system according to claim 10, wherein said periodically flushing means comprise a high pressure saline bag and a stopcock.

* * * * *